US006562997B2

United States Patent
Sikkenga et al.

(10) Patent No.: US 6,562,997 B2
(45) Date of Patent: May 13, 2003

(54) PRODUCTION OF HIGH PURITY AROMATIC CARBOXYLIC ACID BY OXIDATION IN BENZOIC ACID AND WATER SOLVENT

(75) Inventors: David L. Sikkenga, Wheaton, IL (US); Alpen K. Pandya, Naperville, IL (US); Ian C. Zaenger, Naperville, IL (US); Kenneth J. Abrams, Naperville, IL (US); Thomas M. Bartos, Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 09/766,192

(22) Filed: Jan. 19, 2001

(65) Prior Publication Data

US 2001/0041811 A1 Nov. 15, 2001

Related U.S. Application Data

(60) Provisional application No. 60/177,429, filed on Jan. 21, 2000.

(51) Int. Cl.[7] ........................ C07C 51/16; C07C 51/255
(52) U.S. Cl. ........................ 562/413; 562/416; 562/417
(58) Field of Search ........................ 562/416, 417, 562/413

(56) References Cited

U.S. PATENT DOCUMENTS 4,081,464 A   3/1978   Marsh et al.
5,292,934 A   3/1994   Sikkenga et al.
5,612,007 A * 3/1997   Abrams et al. ............. 422/189
5,723,656 A   3/1998   Abrams

FOREIGN PATENT DOCUMENTS

GB          1204184        9/1967
WO       WO 98/38150   *  9/1998
WO          WO07970        2/2000

* cited by examiner

Primary Examiner—Richard L. Raymond
Assistant Examiner—Zachary C. Tucker
(74) Attorney, Agent, or Firm—Stephen L. Hensley

(57) ABSTRACT

Processes for the production of aromatic carboxylic acids is disclosed. The aromatic acids are produced by the liquid phase oxidation of a suitable acid precursor in a reaction medium comprising benzoic acid. According to one embodiment, the oxidation is carried out under plug-flow reaction conditions in a plug-flow reactor. The plug-flow conditions can be achieved by the use of a series of continuous stirred tank reactors. In another embodiment, the oxidation is carried out in two continuous stirred tank reactors fluidly connected in series. The preferred oxidation products are terephthalic acid, isophthalic acid, trimellitic acid, 2,6-naphthalene dicarboxylic acid, 1,5-naphthalene dicarboxylic acid, 2,7-naphthalene dicarboxylic acid and phthalic acid.

44 Claims, 2 Drawing Sheets

US 6,562,997 B2

PRODUCTION OF HIGH PURITY AROMATIC CARBOXYLIC ACID BY OXIDATION IN BENZOIC ACID AND WATER SOLVENT

This application claims the benefit of U.S. provisional application No. 60/177,429 filed Jan. 21, 2000.

FIELD OF THE INVENTION

This invention relates to the production of aromatic carboxylic acid by the liquid phase oxidation of a corresponding aromatic compound having two or three oxidizable ring substituents. Specifically, this invention relates to a process for the production of aromatic carboxylic acid in by the liquid phase oxidation of a correspond aromatic compound having two or more oxidizable ring substituents wherein the oxidation solvent comprises benzoic acid and water and the process yields aromatic carboxylic acid with reduced impurity levels.

BACKGROUND OF THE INVENTION

Aromatic carboxylic acids are useful chemical compounds and are raw materials for a wide variety of manufactured articles. The most widely used commercial processes for the production of aromatic carboxylic acids involve the catalytic liquid-phase oxidation of a suitable aromatic feedstock under elevated pressure and temperature conditions. For example, ortho-xylene is oxidized to produced phthalic acid ("PA"), meta-xylene is oxidized to produce isophthalic acid ("IA"), para-xylene is oxidized to produce terephthalic acid ("TA"), 2,6-dimethynaphthalene is oxidized to produce 2,6-naphthalene dicarboxylic acid ("NDA") and pseudocumene is oxidized to produce trimellitic acid ("TMLA"). These processes may be catalyzed by one or more heavy metal compounds, such as cobalt, manganese, zirconium, cerium or mixtures thereof. In addition, the oxidation reaction is usually promoted one or more promoter compounds, for example elemental bromine.

TA is likely the most widely produced aromatic carboxylic acid. TA is manufactured on a world-wide basis in amounts exceeding 10 billion pounds per year. A single manufacturing plant can produce 100,000 to more than 750,000 metric tons of terephthalic acid per year. TA is used, for example, to prepare polyethylene terephthalate, from which polyester fibers for textile applications and polyester film for packaging and container applications are made. Although there are competing processes, TA is most often produced by the high pressure, exothermic oxidation of para-xylene in a liquid-phase reaction using air or other source of molecular oxygen as the oxidant and catalyzed by one or more heavy metal compounds and one or more promoter compounds.

Methods for oxidizing para-xylene and other aromatic compounds using such liquid-phase oxidations are well known in the art. For example, Saffer in U.S. Pat. No. 2,833,816 discloses a method for oxidizing aromatic feedstock compounds to their corresponding aromatic carboxylic acids. Central to these processes for preparing aromatic carboxylic acids is employing an oxidation catalyst comprising a heavy metal component and a source of bromine in a liquid-phase reaction mixture including a low molecular weight monocarboxylic acid, such as acetic acid, as part of the reaction solvent. A certain amount of water is also present in the oxidation reaction solvent. Water is also formed as a result of the oxidation reaction. Although various means can be used to control the temperature of the highly exothermic oxidation reaction, it is generally most convenient to remove heat by allowing the solvent to vaporize, i.e. boil, during the oxidation reaction. Gaseous effluent from the oxidation reaction generally comprises steam, monocarboxylic acid, an ester thereof, carbon dioxide, carbon monoxide and bromine which, depending on the aromatic feedstock compound used, is mainly in the form of one or more alkyl bromide compounds, such as methyl bromide. Methyl bromide is toxic and, if discharged into the atmosphere, is believed to contribute to depletion of atmospheric ozone. It is therefore important to avoid discharge of methyl bromide into the atmosphere. Additionally, when compressed air is used as the source of molecular oxygen, the gaseous effluent contains nitrogen gas and unreacted oxygen.

In conventional manufacturing processes, TA undergoes catalytic purification to reduce the amount of impurities found therein. Purified Terephthalic Acid ("PTA"), from which fibers, bottles, films etc. are made, is obtained by the catalytic purification of crude terephthalic acid ("TA") generated by the liquid-phase oxidation of para-xylene.

Typically, after the TA is formed by oxidation, it is crystallized and separated from its mother liquor which comprises catalyst components, acetic acid and a variety of intermediates and by-products. The crystallized TA contains a number of impurities, such as 4-carboxybenzaldehyde ("4-CBA") and colored impurities, which are measured by the optical density (light absorption) at 400 nm ("OD400"). These impurities cause undesired effects in the polyester resin. Therefore the TA must be purified.

In a typical purification process, the crystallized TA is dissolved in deionized water at temperatures of from about 250° C. and upward. The solution is then contacted with molecular hydrogen in the presence of a hydrogenation catalyst. The solution is then cooled to crystallized the purified terephthalic acid which is then recovered, washed and dried. Using conventional processes, TA usually contains about 2000 to about 5000 ppm of 4-CBA and OD400 values of approximately 0.1. And PTA typically contains between less than about 75 ppm of 4-CBA and OD400 values of approximately 0.01.

Also, in use today are liquid-phase processes that produce Medium Grade Terephthalic Acid known as MTA. MTA can be used in many of the same applications as PTA, for example, fibers and films. MTA usually contains from about 100 to about 500 ppm of 4-CBA and may have OD400 values slightly greater than about 0.01. Although MTA contains more 4-CBA than PTA, it is produced by substantially the same oxidation process with no subsequent purification.

Conventional processes for the production of IA, PA, NDA and TMLA are similar to that for TA. In each case, the process involves the liquid-phase oxidation of an appropriate aromatic feedstock. Like the TA processes, the aromatic acids obtained from the oxidation contain impurities the level of which is reduced by some type of purification process. In the case of TMLA, the acid is often further processed through dehydration to form trimellitic anhydride.

In general, an appropriate feedstock is a benzene having two appropriately positioned oxidizable ring substituents in the case of TA, IA and PA. For TMLA a suitable feedstock is a benzene ring having oxidizable ring substituents in the 1, 2 and 4 positions. For NDA production a suitable feedstock is naphthalene having oxidizable ring substituents in the 2 and 6 positions.

What is needed is a process for the production of aromatic dicarboxylic or tricarboxylic acid in which the production of toxic methyl bromide production is minimized. The current invention provides a process for the production of aromatic dicarboxylic or tricarboxylic acid in which the formation of methyl bromide substantially reduced relative to conventional processes.

In addition, the current invention provides a process for the production of aromatic dicarboxylic or tricarboxylic acid in which catalytic purification is largely optional. As in one embodiment, to TA produced is suitable for direct conversion to PET without a separate purification step. Other advantages of the invention will become apparent upon reading the following detailed description and appended claims.

SUMMARY OF THE INVENTION

The current invention provides a continuous process for the production of aromatic carboxylic acid by the liquid phase oxidation of an aromatic feedstock with oxygen in a reaction medium comprising the aromatic feedstock, an oxidation promoter, heavy metal catalyst and solvent, the solvent comprising benzoic acid and water, wherein the oxidation is carried out in the reaction zone of a plug flow reactor and wherein at least a portion of the aromatic acid produced crystallizes in the reaction zone. In one embodiment, the oxidation promoter is bromine. In another embodiment, the heavy metal catalyst comprises cobalt, manganese, zirconium, cerium or mixtures thereof. As much as 10%, 15%, 25% or more, by weight, of the aromatic acid may crystallize from the reaction medium in the reaction zone. The oxygen required for the current process is supplied by an oxygen-containing stream which may comprise air or any other suitable oxygen-containing gas. Importantly, the current invention may be used to produce phthalic acid, terephthalic acid, isophthalic acid, 2,6-naphthalene dicarboxylic acid, 1,5-naphthalene dicarboxylic acid, 2,7-naphthalene dicarboxylic acid, trimellitic acid or mixtures thereof depending on the composition of the aromatic feedstock.

In one aspect of the current invention, the solvent ratio in the reaction medium as it enters the reaction zone is from about 1 to about 40. As used herein the solvent ratio is determined as follows:

$$\text{SOLVENT RATIO} = \frac{\text{WEIGHT OF SOLVENT}}{\text{WEIGHT OF AROMATIC FEEDSTOCK}}$$

Preferably, the solvent ratio in the reaction medium when it enters the reaction zone is from about 2 to about 30.

The use of benzoic acid as part of the solvent serves to substantially reduce or eliminate the production of methyl bromide relative to conventional process in which an aliphatic acid, e.g. acetic acid, is used. In the current invention, the solvent comprises from about 5% to about 60% water by weight. Preferably, the solvent comprises from about 10% to about 40% water by weight.

Plug flow reaction conditions are employed to reduce the level of oxidation intermediates, such as 4-CBA, in the reaction zone effluent. By "plug flow reactor" we mean reactor conditions under which the aromatic reactants are prevented from exiting the reaction zone in a residence time significantly shorter than the average residence time of the reactor charge. Importantly, the plug flow reactor of the current invention may comprise a series of two or more continuous stirred tank reactors. The use of a series of continuous stirred tank reactors to achieve plug flow conditions is a common technique recognized and frequently used by those of ordinary skill in the art.

With regard to the current invention, the residence time of the reaction medium in the reaction zone can be optimized to allow for more complete oxidation of the aromatic feedstock relative to conventional processes. Accordingly, the aromatic carboxylic acid obtained from the reaction zone effluent contains lower levels of oxidation intermediates when compared to the oxidation effluent of a conventional process. When the current process is used to produce TA, the amount of 4-CBA in the TA obtained from the reaction medium after the reaction zone is sufficiently low such that a separate purification step is not needed before the TA is converted into PET. Preferably, the amount of 4-CBA in the TA is less than about 500 ppm.

As mentioned previously, the oxidation reaction is highly exothermic. The current invention contemplates adiabatic reaction conditions. Accordingly, no heat is removed from the reaction zone external means. Moreover, the reaction medium may boil thereby generating an off-gas stream that may comprise water vapor, benzoic acid, carbon monoxide, carbon dioxide, oxygen and other gaseous components. This off-gas may be processed and treated using a variety of methods known the those of ordinary skill in the art.

In another embodiment, the current invention also provides a continuous process for the production of a aromatic carboxylic acid by the liquid phase oxidation an aromatic feedstock comprising: (a) providing a reaction medium comprising aromatic feedstock, heavy metal catalyst, a source of bromine, and solvent comprising benzoic acid and water, wherein the aromatic feedstock comprises a benzene having two oxidizable alkyl ring substituents or a naphthalene having two oxidizable alkyl ring substituents and wherein the solvent ratio in the reaction medium is in the range from about 1 to about 30; (b) contacting at least a portion of the reaction medium with an oxygen-containing gas in a first continuous stirred tank reactor thereby generating a product comprising crystalline aromatic carboxylic acid in a liquid medium comprising carboxylic acid, water, heavy metal catalyst, bromine, benzoic acid, oxidation intermediates and by-product compounds; (c) transferring at least a portion of the product to a second continuous stirred tank reactor wherein at least a portion of the product is contacted with an oxygen-containing gas whereby a substantial portion of the oxidation intermediates are oxidized to aromatic carboxylic acid.

According to this embodiment of the current invention, the liquid phase oxidation takes place in two stages, the second stage being useful to complete the oxidation of a substantial portion of oxidation intermediates to carboxylic acid. The crystallized carboxylic acid may comprise about ten percent or more of the carboxylic acid produced in the first continuous stirred tank reactor. The solvent ratio in the first continuous stirred tank reactor is preferably less than about 20. Preferably, the solvent comprises about 5% to about 60% water, by weight, more preferably from about 10% to about 40% water. The preferable aromatic feedstock are selected from the group consisting of para-xylene, meta-xylene, ortho-xylene, 2,6-dimethylnaphthalene or mixtures thereof.

Similar to the plug flow embodiment discussed above, this embodiment of the current invention contemplates adiabatic operation of the first and second continuous stirred tank reactors. Therefore, gaseous off-gas streams are generated. These gaseous off-gas streams comprise water, carbon dioxide, oxygen, carbon monoxide and benzoic acid. When air is used and the oxygen-containing gas, these overhead off-gas streams also comprise nitrogen and other non-condensible components. Importantly, the off-gas stream from each reactor may be treated separately or the streams may be combined into one combined stream and treated as such.

In conventional processes for the production of carboxylic acid in which aliphatic acid, e.g. acetic, solvent is used, the gaseous overhead is stream is treated to remove methyl bromide and other environmental bad actors generated by the oxidation reaction, and to recover desirable components which may be returned to the oxidation reaction. These treatment and recovery operations typically involve fractionation, scrubbing, and catalytic oxidation. In addition, energy recovery schemes, such as those disclosed in co-owned U.S. Pat. Nos. 5,612,007 and 5,723,656 both to Abrams and the teachings of which are incorporated herein by reference, may be employed to recover energy generated by the exothermic oxidation reaction by proper handling of the off-gas. In any event, any off-gas recovery/treatment system necessarily involves separating water from the solvent acid and removing environmentally offensive components by scrubbing or catalytic oxidation.

The use of benzoic acid as a solvent component serves substantially reduce the complexity of the processes and equipment needed to treat or recover off-gas components. First, water and benzoic acid are more easily separated because of difference in their respective boiling points versus, for example, water and acetic acid. Therefore, the complexity of the fractionation of the acid and water in the off-gas is substantially reduced. Secondly, the amount of bromides, e.g. methyl bromide, generated is minimized thereby reducing the amount of equipment and processes needed to treat the off-gas to remove this component and the risk of environmental damage.

The operating conditions in each continuous stirred tank reactor may be determined by those of ordinary skill in the art without undue experimentation depending on the level of oxidation intermediates desired in the end product stream. The temperature in the first continuous stirred tank reactor may be in the range from about 160° C. to about 230° C., preferably in the range from about 180° C. to about 220° C. The pressure in the first continuous stirred tank reactor is preferably in the range from about 200 psig to about 500 psig, more preferably from about 300 psig to about 450 psig. The temperature in the second continuous stirred tank reactor may be in the range from about 180° C. to about 260° C., preferably in the range from about 190° C. to about 220° C. The pressure in the second continuous stirred tank reactor is preferably in the range from about 200 psig to about 500 psig, more preferably in the range from about 300 psig to about 450 psig. In any event, the pressure and temperature profiles of both reactors are generally determined in such away as to ensure that the oxidation reaction takes place in the liquid phase.

When the aromatic feedstock is para-xylene and the aromatic dicarboxylic acid produced is terephthalic acid, the level of the oxidation intermediate 4-CBA in the product is greater than about 3000 ppm. Preferably, at least about 85% of the 4-CBA present in the product is further oxidized in the second continuous stirred tank reactor. More preferably about 90% to about 98% of the 4-CBA in the product is further oxidized to terephthalic acid in the second continuous stirred tank reactor.

The fluid effluent from the second continuous stirred tank reactor may be sent to a crystallizer wherein most of the dicarboxylic acid in the liquid medium is crystallized thereby forming a crystallizer effluent slurry comprising crystallized solid dicarboxylic acid and mother liquor. The crystallizer effluent stream is then transferred to a liquid/solid separation system whereby the dicarboxylic acid is recovered and subsequently dried. The separated mother liquor may then be handle according to conventional methods.

In yet another embodiment, the current invention also provides a continuous process for the production of a aromatic tricarboxylic acid by the liquid phase oxidation an aromatic feedstock comprising: (a) providing a reaction medium comprising aromatic feedstock, heavy metal catalyst, a source of bromine, and solvent comprising benzoic acid and water, wherein the aromatic feedstock comprises a benzene having three oxidizable alkyl ring substituents and wherein the solvent ratio in the reaction medium is in the range from about 2 to about 30; (b) contacting at least a portion of the reaction medium with an oxygen-containing gas in a first continuous stirred tank reactor thereby generating a product stream comprising aromatic tricarboxylic acid in a liquid medium comprising water, heavy metal catalyst, bromine, benzoic acid, oxidation intermediates and by-product compounds; (c) transferring at least a portion of the product stream to a second continuous stirred tank reactor wherein at least a portion of the product stream is contacted with an oxygen-containing gas whereby a substantial portion of the oxidation intermediates are oxidized to aromatic tricarboxylic acid. According to this embodiment of the current invention, the liquid phase oxidation takes place in two stages, the second stage being useful to complete the oxidation of a substantial portion of oxidation intermediates to tricarboxylic acid. The solvent ratio in the first continuous stirred tank reactor is preferably in the range from about 2 to about 20. Preferably, the solvent comprises about 5% to about 60% water, by weight, more preferably from about 10% to about 40% water.

DETAILED DESCRIPTION OF THE DRAWINGS

Figure 1:
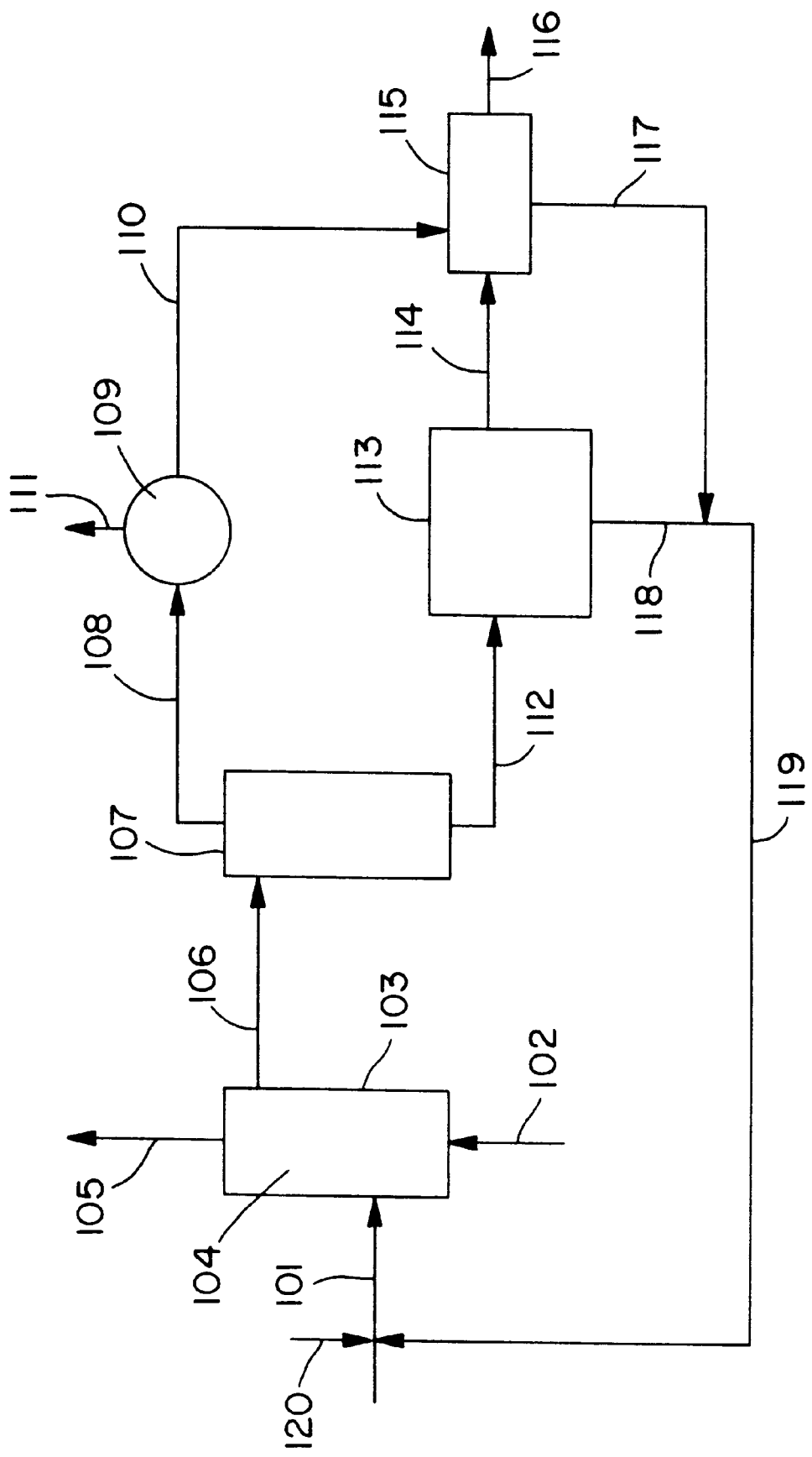
FIG. 1 is a schematic drawing of one embodiment of the process of the current invention incorporating a plug flow reactor.

Turning first to FIG. 1, there illustrated is an embodiment of the current invention in which the reaction zone operates under plug flow conditions. Reaction medium stream 101 and oxygen-containing gas stream 102 are directed to reactor 103. Reaction medium stream 101 comprises aromatic feedstock, heavy metal catalyst, and oxidation promoter in solvent comprising benzoic acid and water. The aromatic feedstock is selected from the group consisting of benzenes have two or three oxidizable ring substituents and naphthalenes having at least one oxidizable ring substituent on each of its aromatic rings. Preferably, the aromatic feedstock comprises para-xylene, ortho-xylene, meta-xylene, pseudocumene, 1,5-dimethylnaphthalene, 2,6-dimethylnaphthalene, 2,7-dimethylnaphthalene or mixtures thereof. The heavy metal catalyst preferably comprises cobalt, manganese, zirconium, cerium or mixtures thereof. The oxidation promoter is preferably a source of bromine. Oxygen-containing gas stream 102 comprises any suitable oxygen-containing gas, preferably air.

Reactor 103 has a reaction zone 104 disposed therein. The temperature and pressure conditions in reactor 103 are selected in order to maintain the oxidation reaction in the liquid phase. The pressure within reactor 103 is preferably within the range from about 200 psig to about 500 psig, more preferably within the range from about 300 psig to about 450 psig. The temperature within reactor 103 is preferably within the range from about 180° C. to about 230° C., more preferably within the range from about 190° C. to about 220° C., most preferably within the range from about 190° C. to about 210° C. The solvent ratio in reaction medium in reaction zone 104 is maintained in the range from about 1 to about 40, preferably in the range from about 2 to about 30. All ranges provided in this specification are inclusive.

Reactor 103 is operated under plug flow conditions such that the aromatic reactants therein experience substantially the same residence time within reaction zone 104. In reaction zone 104, the aromatic feedstock is oxidized to a corresponding carboxylic acid.

The carboxylic acid generated in reactor 103 may not be completely soluble in the reaction medium. Therefore, as the carboxylic acid is generated at least a portion of it begins to crystallize from the reaction medium in reaction zone 104. For example, as much as 10%, 15% or even 25% of the carboxylic acid generated may crystallize in reaction zone 104.

Recovery of the carboxylic acid product may be achieved by substantially conventional means. In FIG. 1, the carboxylic acid recovery scheme depicted it similar to the conventional means used in the production of terephthalic acid and isophthalic acid. With reference to FIG. 1, reactor effluent 106 comprises crystallized carboxylic acid in a liquid medium comprising dissolved carboxylic acid, water, benzoic acid, heavy metal catalyst, oxidation promoter, oxidation intermediates, and by product compounds. The level of oxidation intermediates present in reactor effluent 106 is minimized because the plug flow oxidation conditions allow the oxidation reaction to go to substantial completion. Reactor effluent 106 is directed to crystallizer 107 wherein the a substantial portion of the dissolved carboxylic acid is crystallized. Crystallizer 107 is preferably a flash crystallizer wherein the pressure of reactor effluent 106 is substantially reduced almost instantaneously thereby facilitating the crystallization of the dissolved carboxylic acid.

Because of the volatility differences of water and benzoic acid, a significant fraction of the water present in the reactor effluent is selectively vaporized during depressurization in the crystallizer. For some aromatic carboxylic acids, e.g. TA, the solubility decreases with decreasing water in benzoic acid. Accordingly, the depressurization facilitates crystallization of the carboxylic acid by the combined effects of cooling of the reactor effluent and decreasing the solubility of the carboxylic acid in the remaining liquid medium by selective vaporization of water.

The crystallization process in crystallizer 107 generates crystallizer gaseous overhead stream 108 and crystallizer effluent 112. In that crystallizer gaseous overhead stream 108 comprises primarily high-pressure steam, it can be directed to energy recovery means 109 wherein the steam is condensed to form water stream 110. The non-condensible components of crystallizer gaseous overhead stream 108 are purged from the system in purge stream 111. Purge stream 111 may be subject to further processing well known to those of ordinary skill in the art.

Crystallizer effluent 112 comprises crystalline carboxylic acid in a liquid comprising benzoic acid, heavy metal catalyst and oxidation promoter. Crystallizer effluent 112 is directed to liquid/solid separation means 113 wherein the crystallized carboxylic acid is separated from a substantial portion of the liquid components of crystallizer effluent 112. Liquid/solid separation means 113 comprises, for example, at least one centrifuge or at least one rotary pressure filter. An advantage of the current invention is that the liquid component of the crystallizer effluent 112, primarily benzoic acid, has low volatility with a boiling point of 484° F. This makes it possible for the liquid/solid separation to take place at elevated temperatures resulting in increased solubility of impurities that may otherwise crystallize with the carboxylic acid.

Solid effluent 114 comprises crystalline carboxylic acid and from about 10% to about 30% benzoic acid, and is directed to washing means 115. In washing means 115, the crystalline carboxylic acid is washed to remove benzoic acid present therein. This washing may be accomplished, for example, by reslurrying the crystalline carboxylic acid with water provided from water stream 110 followed by liquid/solid separation. The resultant product 116 is, for example, a water wet filter cake that can be dried and stored.

Wash mother liquor 117 from washing means 115 comprises benzoic acid and water. Wash mother liquor 117 may be combined with separation mother liquor 118 resulting in mother liquor recycle 119 which is directed back to reactor 103. Importantly, the elevated temperature at which liquid/solid separation takes place in liquid/solid separation means 113 causes the separation mother liquor 118 to be provided at elevated temperatures thereby allowing mother liquor recycle 119 to be recycled to reactor 103 with little or no preheating. Optionally, a portion of mother liquor recycle 119 may be purged to prevent build up of impurities in reactor 103.

Generally, it will be necessary in continuous operation to add heavy metal catalyst, oxidation promoter and other reaction medium components in order to replace the small amounts of these materials lost during processing. Make-up catalyst 120 may be provided to replace catalyst and oxidation promoter. Importantly, because the solvent used comprises benzoic acid, the necessary benzoic acid make-up may be provided by supplying toluene or other monoalkylbenzene as part of the reaction medium. The toluene or other monoalkylbenzene is converted to benzoic acid in reactor 103.

The oxidation reaction is highly exothermic. The current invention contemplates adiabatic conditions in which the reaction medium is allowed to boil, thereby generating high pressure gaseous overhead stream 105. High pressure gaseous overhead stream 105 comprises water, carbon dioxide, carbon monoxide, benzoic acid and other oxidation by-products. When oxygen-containing gas stream 102 comprises air, gaseous overhead stream 105 further comprises nitrogen, argon and other non-condensible gases.

Treatment of the high pressure gaseous overhead stream may involve directing high pressure gaseous overhead stream 105 to a high efficiency separation apparatus (not shown in FIG. 1) in which at least about 95% of the benzoic acid is removed and sent back to the oxidation reactor. Energy may be recovered from the overhead stream from the high efficiency separation apparatus. This technique of efficient operation is taught in co-owned U.S. Pat. No. 5,723,656. Treatment of high pressure gaseous overhead stream 105 may alternatively include condensation of the stream followed by fractionation as taught in European Patent 498,591 the teachings of which are incorporated herein by reference.

Figure 2:
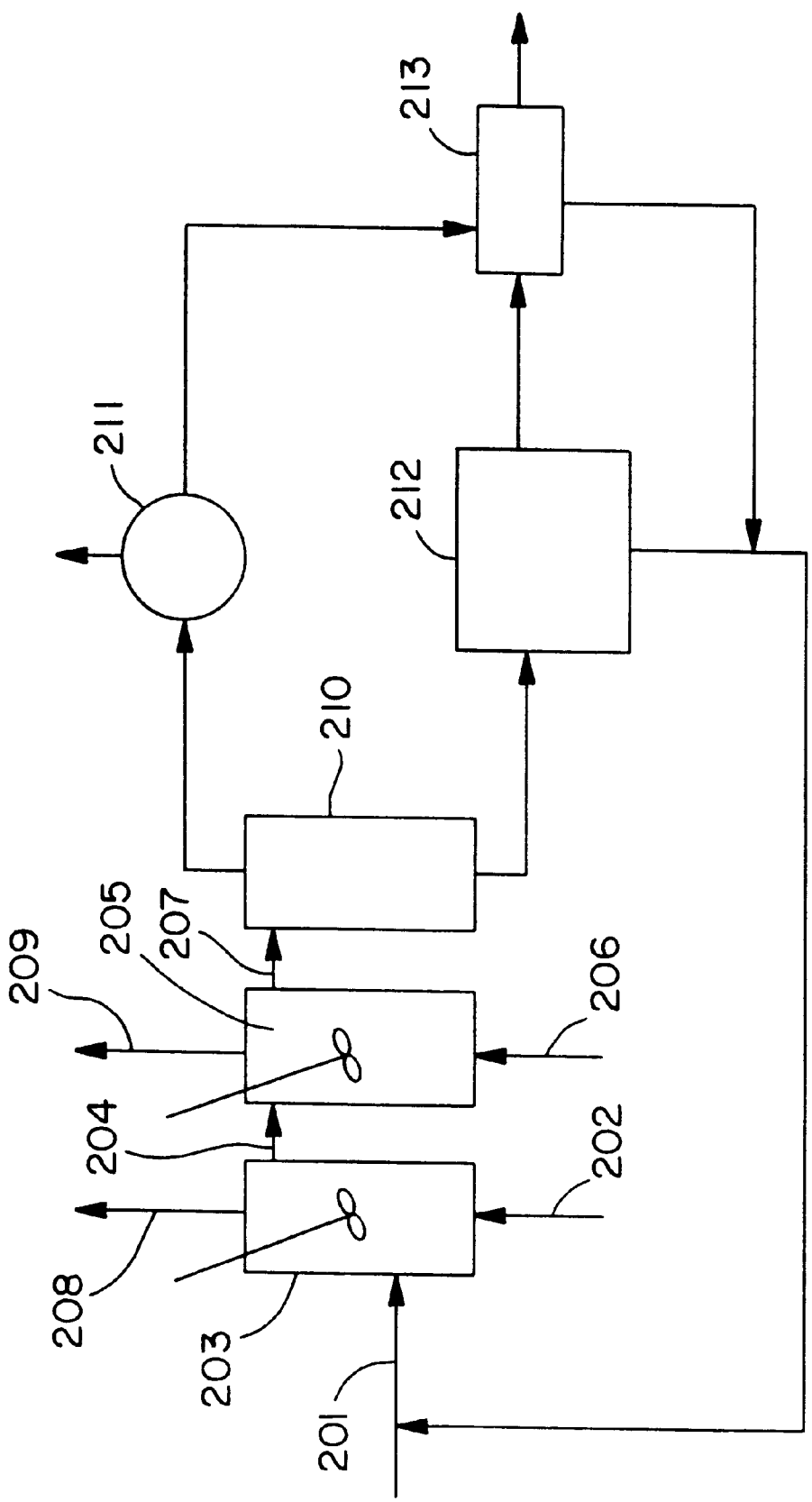
FIG. 2 is a schematic drawing of another embodiment of the process of the current invention incorporating two continuous stirred tank reactors.

Turning now to FIG. 2, there illustrated in schematic form is a process of the current invention incorporating two continuous stirred tank reactors in series. With reference to FIG. 2, reaction medium 201 is and first oxygen-containing gas 202 are directed to first continuous stirred tank reactor 203. Reaction medium 201 comprises aromatic feedstock, heavy metal catalyst and oxidation promoter in a solvent comprising benzoic acid and water.

The aromatic feedstock is selected from the group consisting of benzenes having two or three oxidizable ring substituents and naphthalenes having a least one oxidizable ring substituent on each of its aromatic rings. Preferably, the aromatic feedstock comprises para-xylene, ortho-xylene, meta-xylene, pseudocumene, 1,5-dimethylnaphthalene, 2,6-dimethylnaphthalene, 2,7-dimethylnapthalene or mixtures thereof. The heavy metal catalyst preferably comprises cobalt, manganese, zirconium, cerium or mixtures thereof. The oxidation promoter is preferably a source of bromine. Oxygen-containing gas stream 102 comprises any suitable oxygen-containing gas, preferably air. The solvent ratio in the reaction medium is in the range from about 2 to about 40, preferably in the range from about 4 to about 20. In addition, the solvent comprises from about 5% to about 60% water, preferably from about 10% to about 40% water.

In first continuous stirred tank reactor 203, the aromatic feedstock is oxidized in the liquid phase to aromatic carboxylic acid and a variety of intermediates. First reactor liquid effluent 204 comprises crystallized aromatic carboxylic acid in a liquid medium comprising dissolved carboxylic acid, heavy metal catalyst, bromine, water, benzoic acid, oxidation intermediates and by-product compounds. Preferably, more than about 10%, by weight, of the carboxylic acid produced in first continuous stirred reactor 203 crystallizes in first continuous stirred tank reactor 203.

First reactor effluent 204 is directed to second continuous stirred tank reactor 205. In second continuous stirred tank reactor 205, at least a portion of first reactor effluent 204 is contacted with oxygen supplied by second oxygen-containing gas stream 206, whereby a substantial portion of the oxidation intermediates is oxidized to aromatic carboxylic acid. Second reactor liquid effluent 207 comprises crystallized aromatic carboxylic acid in a liquid medium comprising dissolved carboxylic acid, heavy metal catalyst, bromine, water, benzoic acid, oxidation intermediates and by-product compounds. Relative to first reactor effluent 204, second reactor effluent 207 comprises about 85% less oxidation intermediates, by weight. Moreover, about 85% of the oxidation intermediates present in first reactor effluent 204 is oxidized to carboxylic acid in second continuous stirred reactor 205.

The operating conditions in each continuous stirred tank reactor may be determined by those of ordinary skill in the art without undue experimentation depending on the level of oxidation intermediates desired in the end product stream. The temperature in first continuous stirred tank reactor 203 may be in the range from about 160° C. to about 230° C., preferably in the range from about 180° C. to about 220° C. The pressure in first continuous stirred tank reactor 203 is preferably in the range from about 200 psig to about 500 psig, more preferably from about 300 psig to about 450 psig. The temperature in second continuous stirred tank reactor 205 may be in the range from about 180° C. to about 260° C., preferably in the range from about 190° C. to about 220° C. The pressure in second continuous stirred tank reactor 205 is preferably in the range from about 200 psig to about 500 psig, more preferably in the range from about 300 psig to about 450 psig. In any event, the pressure and temperature profiles of both reactors are generally determined in such away as to ensure that the oxidation reaction takes place in the liquid phase.

When the aromatic feedstock is para-xylene and the aromatic dicarboxylic acid produced is terephthalic acid, the level of the oxidation intermediate 4-CBA in the product slurry is greater than about 3000 ppm. Preferably, at least about 85% of the 4-CBA present in first reactor effluent 204 is further oxidized in second continuous stirred tank reactor 205. More preferably about 90% to about 98% of the 4-CBA in first reactor effluent 204 is further oxidized to terephthalic acid in second continuous stirred tank reactor 205.

Adiabatic operation of first continuous stirred tank reactor 203 and second continuous stirred tank reactor 205 results in the formation of first gaseous effluent 208 and second gaseous effluent 209. Both first gaseous effluent 208 and second gaseous effluent 209 are high pressure gaseous streams and comprise water, carbon dioxide, carbon monoxide, oxygen, benzoic acid and, if the air is the oxygen-containing gas, other non-condensible components such as nitrogen. These gaseous effluents are generally subjected to some type of treatment and/or recovery processes, and may be treated separately or combined into a single stream. First gaseous effluent 208 and second gaseous effluent 209 may be treated, either alone or in combination, in the same manner discussed above with reference to FIG. 1. For example, treatment of first gaseous effluent 208 and second gaseous effluent 209 may involve directing them to a high efficiency separation apparatus (not shown in FIG. 1) in which at least about 95% of the benzoic acid is removed and sent back to the oxidation reactor along with other recovered reactants. Energy may be recovered from the overhead stream from the high efficiency separation apparatus by directing it to an energy recovery means such as an expander. Such energy recovery means may be connected to generator whereby the recovered energy is converted to electrical power.

The carboxylic acid product may be recovered for second reactor effluent 207 in substantially the same manner as discussed above with reference to FIG. 1. As schematically represented in FIG. 2, crystallizer 210, recovery means 211, liquid/solid separation means 212, and washing means 213 all operated in a similar fashion as discussed with regard to FIG. 1 above.

Having described the invention we claim:

1. A process for the production of an aromatic carboxylic acid comprising a liquid phase oxidation of an aromatic feedstock with oxygen in a reaction medium comprising the aromatic feedstock, a promoter, heavy metal catalyst and a solvent comprising benzoic acid and water at a solvent ratio in the range of about 1 to about 40, wherein the oxidation is carried out in the reaction zone of a plug flow reactor and wherein at least a portion of the aromatic acid produced crystallizes from the reaction medium in the reaction zone.

2. The process of claim 1, wherein at least about ten percent, by weight, of the aromatic carboxylic acid crystallizes in the reaction zone.

3. The process of claim 1, wherein at least about fifteen percent, by weight, of the aromatic acid crystallizes in the reaction zone.

4. The process of claim 1, wherein the reaction medium entering the reaction zone comprises toluene or another monoalkylbenzene that can be converted to benzoic acid in the reaction zone.

5. The process of claim 1, wherein the solvent ratio in the reaction medium entering the reaction zone is in the range from about 2 to about 30.

6. The process of claim 1, wherein the aromatic feedstock is a benzene having two oxidizable alkyl ring substituents, a naphthalene having two oxidizable alkyl substituents, or mixtures thereof.

7. The process of claim 6, wherein the aromatic feedstock is selected from the group consisting of para-xylene, meta-xylene, ortho-xylene, 2,6-dimethylnaphthalene, 1,5-dimethylnaphthalene, 2,7-dimethylnaphthalene or mixtures thereof.

8. The process of claim 1, wherein at least twenty percent by weight of the aromatic carboxylic acid crystallizes from the reaction medium while the reaction medium is in the reaction zone.

9. The process of claim 1, wherein at least twenty-five percent by weight of the aromatic carboxylic acid crystallizes from the reaction medium while the reaction medium is in the reaction zone.

10. The process of claim 7, wherein the aromatic feedstock is para-xylene and the aromatic carboxylic acid is terephthalic acid.

11. The process of claim 7, wherein the aromatic feedstock is meta-xylene and the aromatic acid is isophthalic acid.

12. The process of claim 7, wherein the aromatic feedstock is 2,6-dimethylnaphthalene and the aromatic carboxylic acid is 2,6-naphthalene dicarboxylic acid.

13. The process according to claim 1, wherein the promoter comprises bromine.

14. The process according to claim 1, wherein the plug flow reactor comprises a plurality of continuous stirred tank reactors in series, each continuous stirred tank reactor comprising a reactor space whereby the plurality of continuous stirred tank reactors comprises a plurality of reactor spaces, wherein the reaction zone comprises the plurality of reactor spaces.

15. The process according to claim 1, wherein the liquid phase oxidation is carried out under reaction conditions which produce a gaseous high pressure stream comprising water, gaseous by-products, and gaseous benzoic acid and further comprising:
   (a) removing in a high efficiency separation apparatus at least 95 wt. % of the benzoic acid from the gaseous high pressure stream to form a second gaseous high pressure stream comprising water and gaseous by-products formed during the oxidation reaction; and
   (b) directing the second gaseous high pressure stream to a means for recovering energy from the second gaseous high pressure stream.

16. The process of claim 15, wherein the high efficiency separation apparatus is a high efficiency distillation column.

17. The process of claim 16, wherein the high efficiency distillation column comprises at least 5 theoretical plates.

18. The process of claim 15, wherein the means for recovering energy from the second gaseous high pressure stream comprises an expander.

19. The process according to claim 1, wherein the liquid phase oxidation is carried out under reaction conditions which produce a gaseous high pressure stream comprising water, gaseous by-products, and gaseous benzoic acid and further comprising:
   (a) removing in a high efficiency separation apparatus about 95 wt. % of the benzoic acid from the gaseous high pressure stream to form a second gaseous high pressure stream comprising water and gaseous by-products formed during the oxidation reaction; and
   (b) directing the second gaseous high pressure stream to a means for recovering energy from the second gaseous high pressure stream.

20. The process of claim 19, wherein the high efficiency separation apparatus is a high efficiency distillation column.

21. The process of claim 20, wherein the high efficiency distillation column comprises at least 5 theoretical plates.

22. The process of claim 20, wherein the high efficiency distillation column comprises about 5 theoretical plates.

23. The process of claim 16, wherein the high efficiency distillation column comprises about 5 theoretical plates.

24. A process for the production of an aromatic dicarboxylic acid by the liquid phase oxidation of an aromatic feedstock comprising:
   (a) providing a reaction medium comprising an aromatic feedstock, heavy metal catalyst, a source of bromine, and a solvent comprising benzoic acid and water, wherein the aromatic feedstock comprises a benzene having two oxidizable alkyl ring substituents in the meta or para positions or a naphthalene having two oxidizable alkyl ring substituents and wherein the solvent ratio in the reaction medium is in the range from about 1 to about 40;
   (b) contacting at least a portion of the reaction medium with an oxygen-containing gas in a first continuous stirred tank reactor thereby generating a product comprising crystallized aromatic dicarboxylic acid in a liquid medium comprising dissolved dicarboxylic acid, heavy metal catalyst, bromine, water, benzoic acid, oxidation intermediates and by-product compounds; and
   (c) directing the product to a second continuous stirred tank reactor wherein at least a portion of the product is contacted with an oxygen-containing gas whereby a substantial portion of the oxidation intermediates are oxidized to aromatic dicarboxylic acid.

25. The process of claim 24 wherein the aromatic feedstock is selected from the group consisting of para-xylene, meta-xylene, 2,6-dimethylnaphthalene, 1,5-dimethylnaphthalene, 2,7-dimethylnaphthalene or mixtures thereof.

26. The process of claim 24, wherein the aromatic feedstock is para-xylene and the aromatic dicarboxylic acid is terephthalic acid.

27. The process of claim 24, wherein the aromatic feedstock is meta-xylene and the aromatic dicarboxylic acid is isophthalic acid.

28. The process of claim 24, wherein the aromatic feedstock is 2,6-dimethyl naphthalene and the aromatic dicarboxylic acid is 2,6-naphthalene dicarboxylic acid.

29. The process according to claim 25, wherein the promoter comprises bromine.

30. The process according to claim 25, wherein the solvent ratio in the reaction medium is in the range from about 2 to about 30.

31. The process according to claim 25, wherein the solvent ratio in the reaction medium is in the range from about 2 to about 20.

32. The process according to claim 25, wherein a high pressure gas stream comprising water, carbon dioxide, carbon monoxide, oxygen and benzoic acid is generated in the first continuous stirred tank reactor and a second high pressure gas stream comprising water, carbon dioxide, carbon monoxide, oxygen and benzoic acid is generated in the second continuous stirred tank reactor, and further comprising:
   (a) combining the first high pressure gas stream and the second high pressure gas stream to form a gaseous high pressure stream;
   (b) removing in a high efficiency separation apparatus at least 95 wt. % of the benzoic acid from the gaseous high pressure stream to form a second gaseous high pressure stream comprising water and gaseous by-products formed during the oxidation reaction; and (c) directing the second gaseous high pressure stream to a means for recovering energy from the second gaseous high pressure stream.

33. The process of claim 32, wherein the high efficiency separation apparatus is a high efficiency distillation column.

34. The process of claim 33, wherein the high efficiency distillation column comprises at least 5 theoretical plates.

35. The process of claim 32, wherein the means for recovering energy from the second gaseous high pressure stream comprises an expander.

36. The process according to claim 33, wherein the high efficiency distillation column comprises about 5 theoretical plates.

37. The process according to claim 25, wherein a high pressure gas stream comprising water, carbon dioxide, carbon monoxide, oxygen and benzoic acid is generated in the first continuous stirred tank reactor and a second high pressure gas stream comprising water, carbon dioxide, carbon monoxide, oxygen and benzoic acid is generated in the second continuous stirred tank reactor, and further comprising:

(a) combining the first high pressure gas stream and the second high pressure gas stream to form a gaseous high pressure stream;

(b) removing in a high efficiency separation apparatus about 95 wt. % of the benzoic acid from the gaseous high pressure stream to form a second gaseous high pressure stream comprising water and gaseous by-products formed during the oxidation reaction; and (c) directing the second gaseous high pressure stream to a means for recovering energy from the second gaseous high pressure stream.

38. The process of claim 37, wherein the high efficiency separation apparatus is a high efficiency distillation column.

39. The process of claim 38, wherein the high efficiency distillation column comprises about 5 theoretical plates.

40. The process of claim 38, wherein the high efficiency distillation column comprises at least 5 theoretical plates.

41. A continuous process for the production of an aromatic tricarboxylic acid by the liquid phase oxidation of an aromatic feedstock comprising:

(a) providing a reaction medium comprising an aromatic feedstock, heavy metal catalyst, a source of bromine, and solvent comprising benzoic acid and water, wherein the aromatic feedstock comprises a benzene having three oxidizable alkyl ring substituents and wherein the solvent ratio in the reaction medium is in the range from about 1 to about 40;

(b) contacting at least a portion of the reaction medium with an oxygen-containing gas in a first continuous stirred tank reactor thereby generating a product stream comprising aromatic tricarboxylic acid in a liquid medium comprising water, heavy metal catalyst, bromine, benzoic acid, oxidation intermediates and by-product compounds; and (c) transferring at least a portion of the product stream to a second continuous stirred tank reactor wherein at least a portion of the transferred product stream is contacted with an oxygen-containing gas whereby a substantial portion of the oxidation intermediates are oxidized to aromatic tricarboxylic acid.

42. A process for the production of an aromatic carboxylic acid comprising a liquid phase oxidation of an aromatic feedstock comprising trialkylbenzene, ortho-dialkylbenzene or mixtures thereof with oxygen in a reaction medium comprising the aromatic feedstock, a promoter, heavy metal catalyst and a solvent comprising benzoic acid and water, wherein the oxidation is carried out in the reaction zone in a plug flow reactor.

43. The process of claim 42, wherein the solvent ratio of the reaction medium entering the reaction zone is in the range from about 1 to about 40.

44. The process of claim 43, wherein the aromatic feedstock comprises psuedocumene, ortho-xylene or mixtures thereof.

* * * * *